(12) United States Patent
Bach-y-Rita et al.

(10) Patent No.: US 6,430,450 B1
(45) Date of Patent: Aug. 6, 2002

(54) TONGUE PLACED TACTILE OUTPUT DEVICE

(75) Inventors: Paul Bach-y-Rita; Kurt A. Kaczmarek, both of Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/601,717

(22) PCT Filed: Jan. 28, 1999

(86) PCT No.: PCT/US99/01734

§ 371 (c)(1),
(2), (4) Date: Sep. 29, 2000

(87) PCT Pub. No.: WO99/39670

PCT Pub. Date: Aug. 12, 1999

Related U.S. Application Data (60) Provisional application No. 60/073,873, filed on Feb. 6, 1998.

(51) Int. Cl.[7] ............................................... A61N 1/00
(52) U.S. Cl. ..................... 607/134; 379/52; 382/114
(58) Field of Search ............................. 607/2, 134, 47; 600/554; 379/52; 434/112, 114; 382/114

(56) References Cited

U.S. PATENT DOCUMENTS

| | | | |
|---|---|---|---|
| 3,612,061 A | | 10/1971 | Collins et al. ............... 128/418 |
| 4,254,776 A | | 3/1981 | Tanie et al. .................. 128/421 |
| 4,637,405 A | * | 1/1987 | Brenman et al. ........... 128/787 |
| 4,669,459 A | * | 6/1987 | Spiewak et al. ............ 128/136 |
| 5,853,005 A | * | 12/1998 | Scanlon ................. 128/662.03 |
| 5,878,154 A | * | 3/1999 | Schimmelpfennig ........ 382/114 |

FOREIGN PATENT DOCUMENTS

| | | |
|---|---|---|
| EP | 0487027 A1 | 5/1992 |
| WO | WO81/01512 | 6/1981 |
| WO | WO95/13037 | 5/1995 |

OTHER PUBLICATIONS

PCT International Search Report dated May 25, 1999 in PCT Appln. No. PCT/US99/01734.

Kaczmarek, Kurt A., et al., "Electrotactile and Vibrotactile Displays for Sensory Substitution Systems," *IEEE*, 38:1–15 (Jan. 1991).

* cited by examiner

*Primary Examiner*—Jeffrey R. Jastrzab
*Assistant Examiner*—Frances P. Oropeza
(74) *Attorney, Agent, or Firm*—Quarles & Brady LLP (57) ABSTRACT

A mouth stabilized electrode array allows spatially encoded data to be tactily impressed upon the tongue providing an alternative to conventional visual pathways with a more compact size, lower power usage, and more convenient apparatus.

20 Claims, 5 Drawing Sheets

TONGUE PLACED TACTILE OUTPUT DEVICE

CROSS-REFERENCE TO RELATED APPLICATIONS

This application is based on U.S. provisional application No. 60/073,873 filed Feb. 6, 1998 and claims the benefit thereof. This provisional application is hereby incorporated by reference.

STATEMENT REGARDING FEDERALLY SPONSORED RESEARCH OR DEVELOPMENT

This invention was made with United States government support awarded by the following agencies: NIH Grant No: EY10019. The United States has certain rights in this invention.

BACKGROUND OF THE INVENTION

Tactile vision substitution systems (TVSS) are used to deliver image information to the brain via an array of stimulators in contact with the skin in one of several parts of the body, for example, the abdomen, the back, the thigh or the fingertip. Points of the image are mapped to individual stimulators in the array as either vibrations or direct electrical excitation. With training, perceptual judgments normally used for vision such as depth judgment can be applied to these tactile images. A summary of the art in this field is provided in a paper by the present inventors, hereby incorporated by reference, entitled: *Electrotactile and Vibrotactile Displays for Sensory Substitution Systems,* IEEE Transactions on Biomedical Engineering, Volume 38, No. 1, January 1991.

The delay in perception for tactile arrays is less than that for vision. For this reason, TVSS systems are not only promising as rehabilitative strategies for sight-impaired individuals but offer an alternative human/machine interface for sighted individuals, especially where rapid reaction times are required.

Unfortunately, current TVSS systems have been limited in practical application. Mechanical vibrotacter systems in which the stimulators vibrate are bulky and require considerable energy. Electrotactile systems in which the stimulators produce direct electrical stimulation require relatively high voltage, especially in areas of the fingertips, because there are protective layers of skin between skin surface and the skin's sensory receptors. TVSS systems which use the fingertips as a reception site, limit the use of the hands for other tasks whereas systems using a site such as the abdomen require larger arrays, are less convenient, and require a conductive gel for proper operation.

SUMMARY OF THE INVENTION

The present invention provides an improved human/machine interface (HMI) system using the tongue as a stimulation site. The tongue contains a large number of nerve endings, thus permitting the construction of a small array with a high number of stimulators. Preliminary data by the inventors shows that users tend to adapt or accommodate stimulation current over time when that current is applied to the fingertip requiring the stimulation current or voltage to be increased. In contrast, it presently appears that subjects maintain a constant or even slightly decreasing current level for tongue stimulation.

Specifically the present invention provides a tactile stimulation array for the tongue having a mouth part sized to be received and stabilized within the mouth and an array of tactile elements positioned over a lower surface of the mouth part to be in contact with the tongue when the mouth part is received within the mouth. Excitation circuitry communicates with the tactile elements and receives a spatially encoded signal to excite selected ones of the tactile elements according to the spatial encoding.

Thus it is one object of the invention to provide an improved human/machine interface for communicating spatially encoded information, such as but not limited to, image information to the tongue as an alternative to optical displays.

The tactile elements may be electrodes and the excitation circuitry may connect the electrodes to a source of electrical power to excite selected ones of the tactile elements.

Thus it is another object of the invention to make use of the improved electrical sensitivity offered by the tongue both because of the location of the tongue's sensory receptors close to its surface and the presence of saliva as a conductor. Experimentation by the present inventors has suggested that the tongue requires only about three percent of the voltage and far less current than, for example, the fingertip, to achieve equivalent sensation levels.

The spatially encoded signal may include a plurality of data points having defined locations and magnitudes and the excitation circuit may map data points to tactile elements having corresponding locations and excite the tactile elements with an electrical pulse according to a function having the data point magnitude as a range and a value selected from the group of: pulse amplitude, pulse duration, and pulse frequency content.

Thus it is another object of the invention to provide a multi-dimensional display where each point of stimulation may have a varied intensity based on a variety of factors. To the extent that the tongue may distinguish simultaneously between these factors, a multidimensional stimulus may be obtained.

The mouth part may include an upwardly concave plate supporting on its lower surface the tactile elements and sized to fit beneath the hard palate.

Thus it is another object of the invention to provide an array that minimizes interference with tongue function. The tongue is highly mobile and may be moved against and away from a tongue based array as required.

The upwardly concave plate may be flanked at its lateral edges by bite bars wherein the mouth part may be stabilized within the mouth by a pressing of the bite bars between the teeth. Alternatively, a dental retainer design may be used with wire brackets engaging the teeth.

It is thus another object of the invention to allow an array that is easily placed within or removed from the mouth and stabilized there and then removed at will.

The mouth part may be a nipple sized to be stabilized within the mouth of a sucking infant.

Thus it is another object of the invention to allow the array to be adapted for infant use as part of a pacifier or the like to provide needed stimulation for sight impaired babies.

The array may include a receiver communicating with the excitation circuitry in receiving the spatially encoded signal as a radio wave.

It is thus another object of the invention to allow the array to be entirely contained within the mouth without obstructing or cumbersome electrical leads. Because electrical stimulation of the tongue requires only about three percent of the voltage as required by the fingertip and much less current, self-contained battery operation is possible.

The foregoing and other objects and advantages of the invention will appear from the following description. In this description, reference is made to the accompanying drawings which form a part hereof and in which there is shown by way of illustration, the preferred embodiment of the invention. Such embodiment does not necessarily represent the full scope of the invention, however, and reference must be made therefore to the claims for interpreting the scope of the invention.

DETAILED DESCRIPTION OF THE PREFERRED EMBODIMENT

Figure 1:
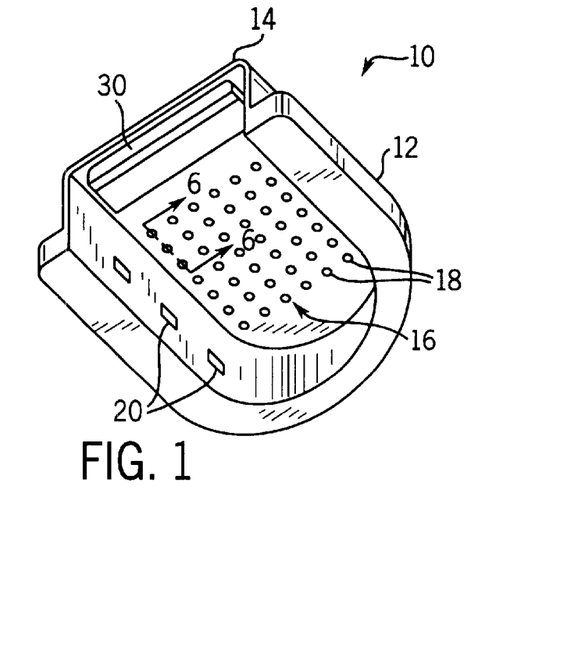
FIG. 1 is a perspective view of a first embodiment of the mouth-based human/machine interface system of the present invention seen from below according to its orientation within a user's mouth.

Referring now to FIG. 1, a first embodiment of the mouth-placed tactile array unit 10 of the present invention includes a horseshoe shaped bite bar 12 sized to be held between the teeth of a typical adult user. An upwardly concave plate 14 spans the distance between the opposing legs of the bite bar 12 so as to fit against the hard palate of a user when the bite bar is held between the teeth. In an alternative embodiment, not shown in FIG. 1, the bite bar may be eliminated and the concave plate 14 used alone in the manner of a dental retainer, shown in FIG. 10, such as is well understood in the art.

In either case, exposed at a lower surface of plate 14 so as to receive the upper surface of the user's tongue, is an array 16 of electrodes 18 arranged generally in parallel rows and columns. It will be understood, however, that a regular spacing of the electrodes 18 need not be adhered to but that a variation in the spacing may occur for example to provide higher spatial resolution for certain portions of the tongue than others. In this regard, several peripheral electrodes 20 may be placed at the edges of the plate 14 to contact the sides of the tongue.

Figure 6:
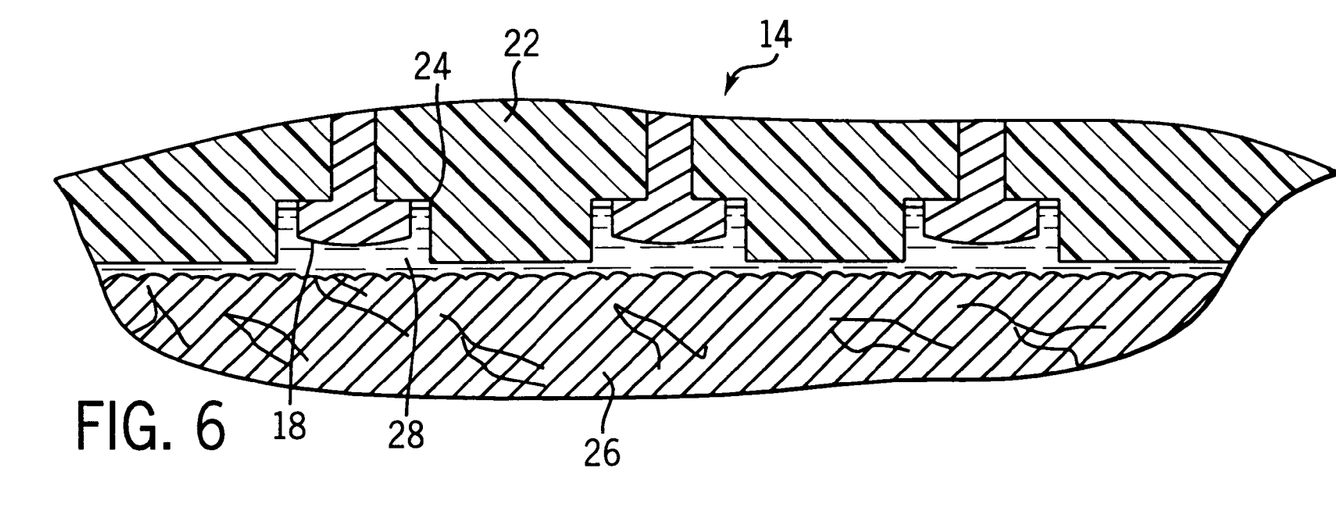
FIG. 6 is a fragmentary cross-sectional view taken along line 6—6 of FIG. 1 showing the placement of the electrodes for stimulation in wells within an insulating plate against which the tongue may be placed.

Referring to FIG. 6 in a first embodiment, each electrode 18 may be surrounded by a matrix of insulating material 22 and placed within a well 24 opening toward the tongue 26 when the tactile array unit 10 is in place within the mouth. The electrodes 18 may be flat-topped stainless steel pins. Individual wells 24 are spaced along the lower surface of the plate 14 by interwell regions of the insulating material 22 to encourage electrical stimulation of the tongue 26 rather than direct current flow between electrodes 18. The wells remove the electrodes 18 from direct contact with the tongue 26 but allow for electrical conduction through saliva 28 which is refreshed by the action of the saliva glands in the mouth.

Figure 7:
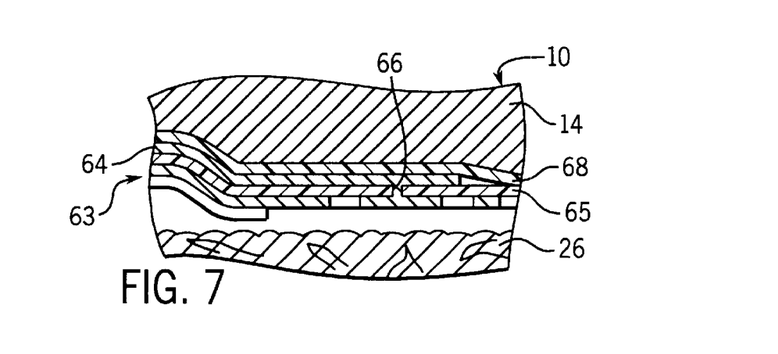
FIG. 7 is a fragmentary cross sectional view taken along lines 6—6 of FIG. 1 showing an alternative embodiment of the electrode design without wells using a flexible printed circuit element.
Figure 8:
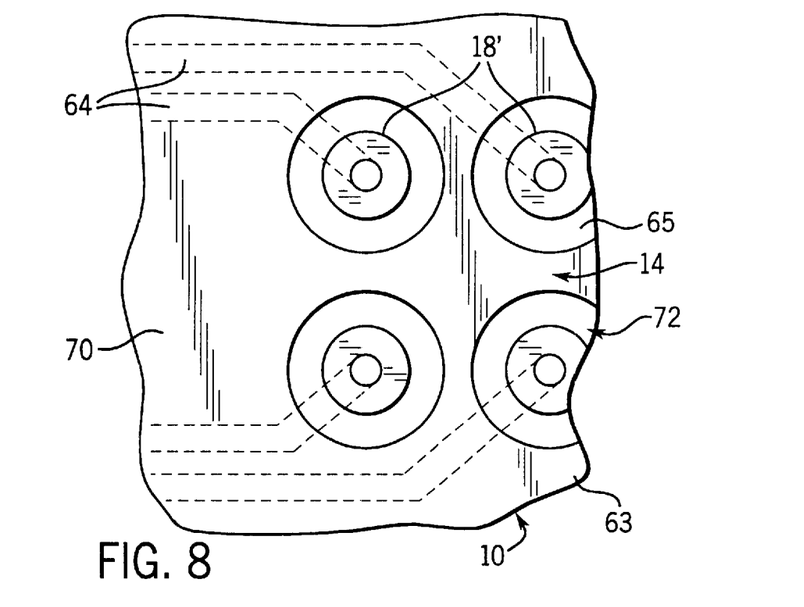
FIG. 8 is a fragmentary plan view of the alternative embodiment of FIG. 7 showing an alternative ground plane construction.
Figure 9:
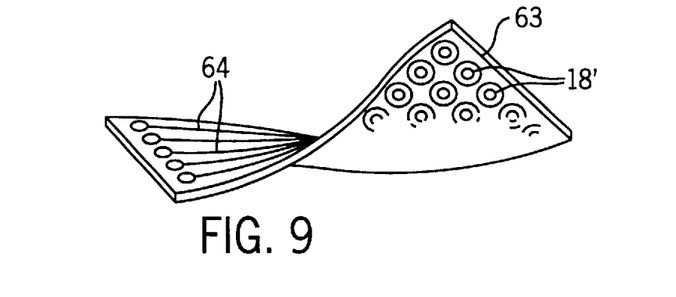
FIG. 9 is a perspective view of the printed circuit element of FIG. 7 removed from the supporting structure.

Referring now to FIGS. 7, 8 and 9, more recent research has suggested that the wells 24 (of FIG. 6) providing a gap between the electrode 18 and the tongue 26 may cause variation in the perceived stimulation and cause adverse mechanical sensation during scanning. Further, because the tongue 26 appears to effectively continuously clean the electrode surface, a completely flat surface may be the best choice for a tongue electrode because saliva cannot build up in gaps. Accordingly, in an alternative embodiment, the wells are eliminated and the surface of the electrodes 18 are made flush or projecting above the insulating material 22.

This latter embodiment shown in FIGS. 7 and 8, the electrodes may be realized as disk shaped pads 18' on the lower surface of a flexible printed circuit board 63 fabricated by standard lithographic techniques known in the art. The electrodes 18' may be etched copper that is then gold plated for bio-compatibility purposes on the surface of an insulating carrier 65 connected to photographically etched connector leads 64 on the other side of the carrier 65 by means of plate-through holes 66 known in the art. The flexible printed circuit board 63 may include an upper insulating layer 68 then embedded in the material of the plate 14.

A ground plane 70 of copper plated with gold may be formed around the electrodes 18' by etching annular gaps 72 about each electrode 18' so that the electrodes 18' are exposed within the gaps and the area outside the gaps 72 is electrically interconnected. The ground plane 70 is connected to provide a return path for electrical current from the electrodes 18'.

The flexibility of the flexible printed circuit board 63 allows increased flexibility of the retainer structure and the promise of improved comfort. The carrier 65 is preferably a polyester to maintain bio-compatibility and provide for minimal water absorption in the oral environment. The electrodes 18 in either embodiment may be stainless steel, titanium, platinum, gold or other bio-compatible conductor.

An example electrode array fabricated in this manner might include 144 electrodes arranged on a 2.3 mm grid to form an array approximately 3 cm square. The size and number of electrodes may be readily varied according to the following guidelines. Generally smaller electrodes can produce a stinging sensation whereas larger electrodes produce a comfortable vibratory perception at the expense of resolution. Presently 0.6 mm electrodes appear to be an acceptable compromise.

Figure 3:
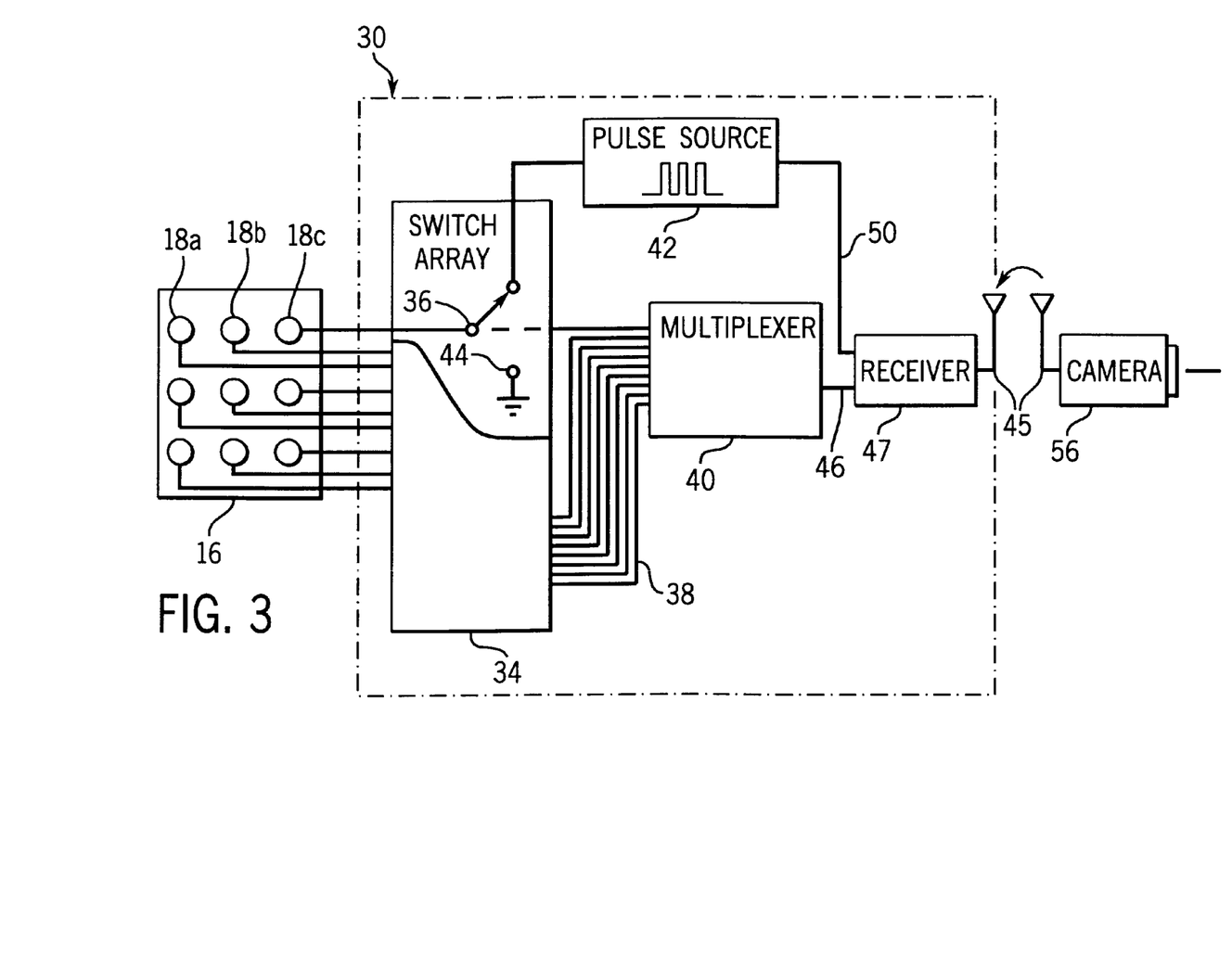
FIG. 3 is a block diagram showing the circuit elements of the embodiments of FIGS. 1 and 2 including a switch array eliminating the need for a continuous ground plane.

Referring now to FIGS. 1 and 3, the electrodes 18 and 20 communicate with a circuit block 30 which may be attached to the plate 14 toward its rear so as to minimize interference with the tongue. A study of retainers for a cross section of the populations suggests that a space of 23 by 15 by 2 mm is available at the back of the plate 14 or two spaces 12 by 9 by 4 mm. Theses spaces may hold a circuit block 30 together with a battery power source (not shown) encapsulated in the same insulating material 22 holding the array 16 and forming the bite bars 12.

As will be described below, the circuit block 30 may communicate with external devices without direct connection thereto, by radio or the like. However, it will be recognized that in an alternative embodiment, the printed circuit material or a cable connected to the conductors of the printed circuit material may extend outside the mouth for direct connection to external processing electronics including the circuit block 30 eliminating the need for in-mouth electronic processing.

In yet another alternative, the circuit block may be incorporated into the plate but may derive its power from an external source, for example, low frequency induction or the like.

Each electrode 18 is connected to a switch array 34 within the circuit block 30. The individual leads connecting the electrodes 18 to the switch array 34 are embedded in an insulated matrix which may be cast or formed about the electronics. Flexible printed circuit technology, as is well understood in the art, may be used to provide interconnections between the electrodes and the electronics in the case where the electrodes are not part of the printed circuits. An insulating cover is placed over the printed circuit wiring so that the latter is sandwiched between the insulating substrate of the printed circuit material and the insulating cover.

The switch array holds a series of solid state switches 36 activated by multiplexer lines 38 from a multiplexer 40. Each solid state switch 36 has a throw connected to one electrode 18 and two poles allowing the throw to be connected to either a pulse source 42 or ground 44 depending on the state of a multiplexer line 38.

The multiplexer 40 controlling the multiplexer lines 38, and the pulse source 42 receive data from a receiver 47 comprising location information 46 and intensity or multidimensional stimulation information 50. When the data is an image, the location information 46 is the location of a pixel value within the image and the intensity information is the intensity of the pixel (when the image is black and white) or the full or partial color value of the pixel.

In operation, the location information 46 is passed to the multiplexer typically based on an implicit ordering of the data points received by the receiver 47. The multiplexer 40 drives selected ones of the multiplexer lines 38 to scan through the electrodes 18 activating one electrode 18 at a time by connecting it through solid state switch 36 to the pulse source 42 and connecting the surrounding electrodes or all other electrodes to ground 44 or other return via their solid state switches 36. The particular electrode 18 being stimulated is successively changed according to the location information so that all electrodes 18 are stimulated in sequence over a period of a scan. Typically the electrodes 18 will be scanned in a raster pattern moving across each row and then returning to the first row at the next column until all electrodes have been scanned. Alternatively the electrodes may be scanned to follow the outline of the object as determined by standard edge detecting morphometric techniques.

Figure 5:
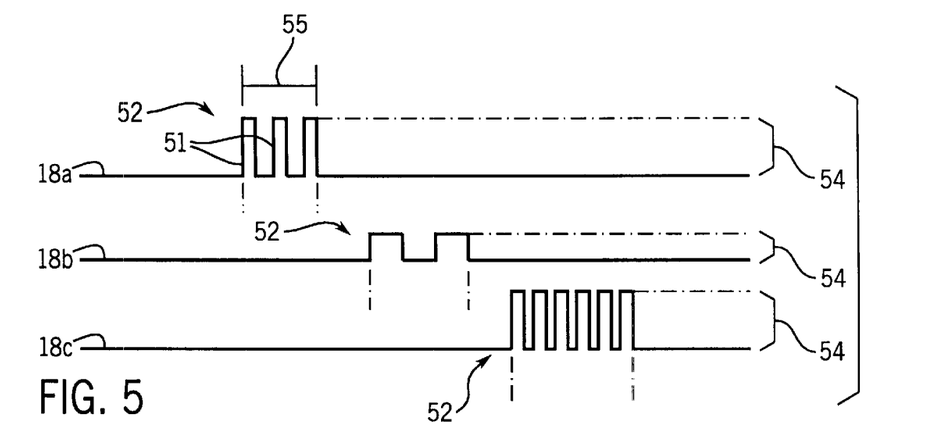
FIG. 5 is a timing diagram showing the delivery of electrical stimulation to three elements of the array of FIGS. 1 or 4 for producing various intensities or multidimensional stimulation.

Referring also to FIG. 5, the amount of stimulation of a given electrode 18 is according to the intensity information 50. In the simplest embodiment, the intensity information is binary and each electrode 18 receives either a monophasic (zero net DC) pulse or no pulse so that simple shapes may be detected. For continuous perception of a "tingle" or "vibration", the electrode is pulsed for 5–50 μs at a rate of 10–400 pulses per second. The pulses may be either current controlled (0.4–4.0 ma) or voltage controlled (5–15 volts). As is understood in the art, current control means the value of the current is defined and the voltage adjusted to produce that current at the tongue, whereas voltage control means the voltage is defined and the current adjusted to produce that voltage at the tongue. In the preferred embodiment, when an electrode 18 is selected by the multiplexer 40, multidimensional intensity information 50 is provided to the pulse source 42 which produces a pulse 52 that may vary in any one of six parameters: pulse height (measured as current or voltage or power), pulse width, the interval between pulses, the number of pulses in a burst, the interval between bursts and the frame rate (i.e., the time between successive scans of the array), as a function of the intensity information 50. These latter five parameters define generally the spectral characteristics of the pulses. All six parameters in the waveforms can, in principle, be varied independently within certain ranges, and may elicit potentially distinct responses.

A pulse source 42 providing suitable pulses (but sized so as to be usable only outside of the mouth, is commercially available from Unitech Research Inc. of Madison, Wisconsin under the tradename VideoTact.

As depicted in FIG. 5, three successive electrodes 18a, 18b and 18c receive a pulse 52 at different times according to their order within the array 16. Each pulse 52 is composed of subpulses 51 which allow simple control of the frequency content and energy of the pulse 52. When a given electrode (e.g., 18a) is being stimulated with a pulse 52, the other electrodes (e.g., 18b and 18c) are in the ground state providing a return path for the electrical current. As depicted, pulse 18b has a lower amplitude 54 and different frequency content than pulse 18a and pulse 18c has a different pulse width 55. To the extent that a trained user may simultaneously distinguish between multiple of these characteristics of amplitude, width and frequency, the pulses 52 may convey multidimensional information in much the same way that the eye perceives color from the independent stimulation of different color receptors.

Although as depicted, each pulse 52 is completed prior to the next electrode 18 being selected by the multiplexer 40, it will be understood that this need not be the case but that the subpulses 51 of the pulses 52 may be interleaved with the subpulses 51 of other pulses 52 to allow faster scanning and lower frequency content pulses 52. Thus, for example, each subpulse 51 may be on the order of 25 microseconds but separated by five milliseconds from the next with the scanning period for an electrode array being less than 5 milliseconds so that the first subpulse 51 for each electrode 18 may occur before the second subpulse 51.

As will be understood in the art, the pulses may be either current or voltage controlled and thus the height depicted in FIG. 5 may be a current or voltage, the two being related by the intrinsic resistance of the tongue electrode interface. Generally both current and voltage limits are imposed on the pulses 52.

It will be understood that other techniques for stimulating the electrodes 18 of the array 16 may be used including those which consider not only the intensity information 50 of individual data points but the intensity information 50 of adjacent data points to provide edge enhancement and the like. Further the mapping of the location information 46 data points and the particular electrodes 18 may be changed so as to provide for a zooming effect in which the image is "enlarged" on the array 16. The amount of zoom could be controlled by an external controller (not shown) or by sensing electrodes in the mouth itself. Particularly with regard to zooming, the peripheral electrodes 20 may be used to provide an indication of a composite intensity information 50 of groups of data points outside of the array 16 so as to, for example, mimic peripheral vision in which a presence of an object off-center may be detected though not fully resolved.

Figure 2:
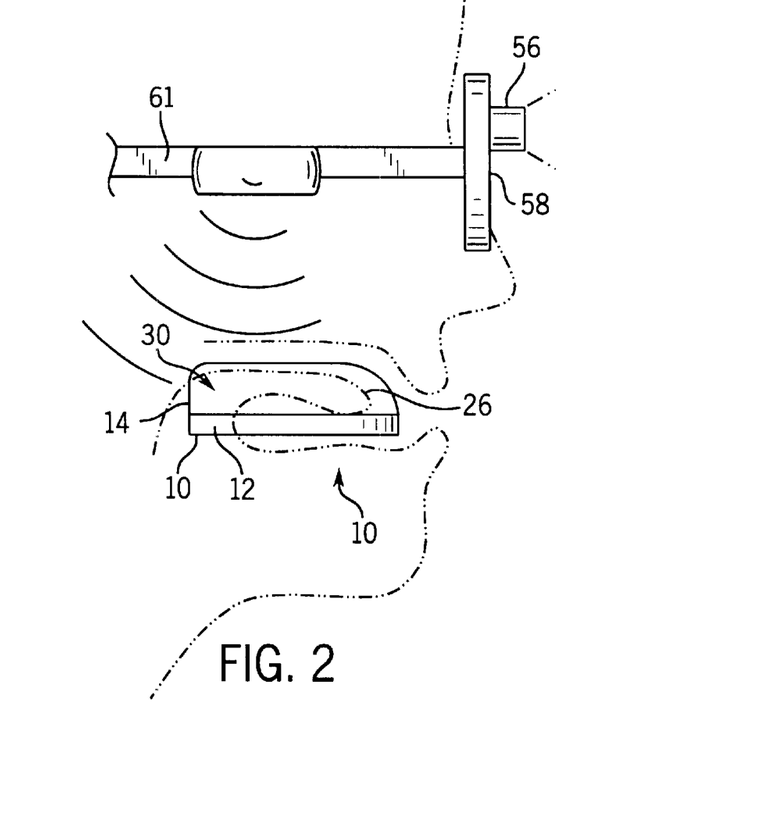
FIG. 2 is a phantom view of a person's head showing placement of the array within the mouth and showing the path of reception via free-space electromagnetic waves of image data from a camera attached to the frame of a pair of glasses.

Referring now to FIG. 2 in a primary embodiment, the visual data received by the receiver may be image data from a miniaturized camera 56, for example, employing a solid state CCD or charge-coupled device type detector. So as to eliminate the need for wires to conduct the image data from the camera 56 to the tactile array unit 10, that data may be transmitted by radio waves via transmitting and receiving antennae 45 according to techniques well known in the art. For example, FM modulated radio frequency signals may be used, or given the close proximity of the camera 56 to the tactile array unit 10, directly modulated low frequency magnetic fields employed. As used herein, radio waves should be held to embrace electromagnetic waves of any frequency. In this case, the wire clips of the retainer structure could serve as an antenna. The camera 56 may be mounted on glass frames 58 and the necessary transmitting electronics supported on a temple 61 of the glass frames to be close to and stably positioned with respect to the circuit block 30 holding the receiver 47. Proximity sensing electronics may be incorporated to conserve battery power for the tactile array unit 10 when it has been removed from the mouth of a user.

Figure 4:
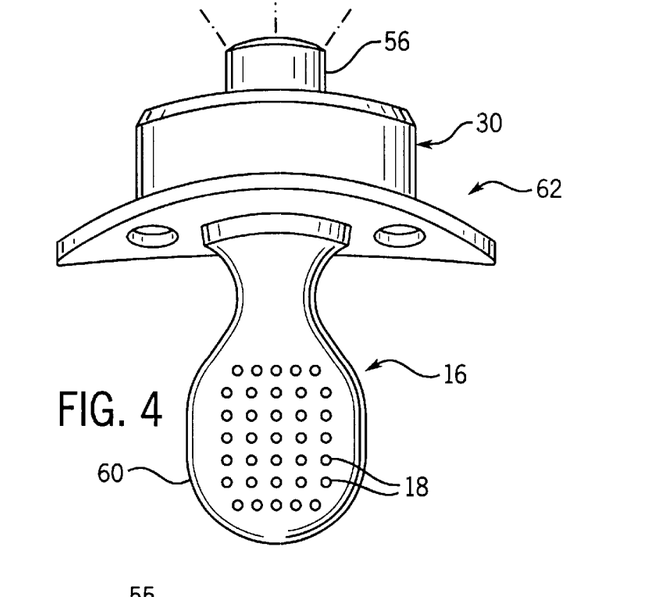
FIG. 4 is a plan view of the bottom of a second embodiment of the human/machine interface system of the present invention in which the array is incorporated into a pacifier for infant use.

In a second embodiment of the invention shown in FIG. 4, the array 16 may have its electrodes 18 exposed from the lower surface of a nipple 60 forming a part of a pacifier 62 having an outward shape similar to ordinary pacifiers well known in the art. In infants, mouth suction control is present at the earliest age and so the nipple 60 could be retained and stabilized within the mouth by such suction action. The camera 56 is positioned on the portion of the pacifier 62 extending out of the baby's mouth normally reserved for a pivoting ring or the like and aligned optically with the long axis of the nipple 60 so that the infant's face is directed toward the source of the image in a natural manner. The circuit block 30 is in this case retained within the body of the pacifier itself a portion of which remains outside the infant's mouth. A direct connection between the camera 56 and the electronics may be had eliminating the need for the radio link. It is believed that the stimulation provided to sight impaired infants could help develop the neural pathways used in image processing. It will be understood that the pacifier configuration may also be used for adults and that the signal providing for zoom or other control of the tactile image or for other output purposes may be provided by the user by biting switches positioned between the teeth.

The cameras described above may employ CMOS type image circuitry to create so-called "active pixel" devices in which image processing may be performed on the same die as that which hold the light sensing array. Such processing may include but is not limited to compression, edge or contrast enhancement, motion detection and even generation of the stimulus pattern to be used by the electrode array. A camera suitable for use with the present invention is commercially available from Austria Micro Systems of Austria and features a matrix of 64 by 64 pixels in a 2 by 2 mm square using conventional 1.3 $\mu$m double metal double poly CMOS process and providing on-chip logarithmic compression with different gains and time constants for static and dynamic illumination so as to mimic the human retina. This camera has demonstrated a dynamic range of about eight orders of magnitude in incident light intensity and a slope ratio of about 30:1 between the static and dynamic cases. Digitization of the signals is accomplished on chip.

Figure 10:
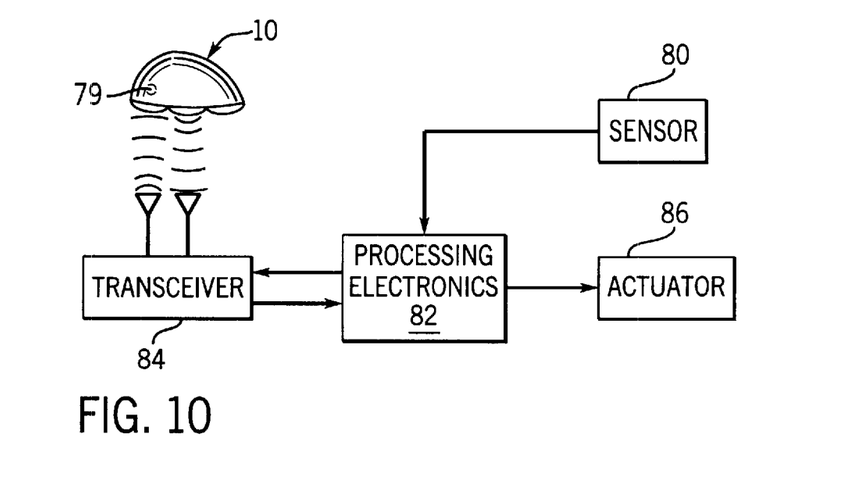
FIG. 10 is block diagram of an alternative embodiment of the mouth-based human/machine interface of the present invention providing for bi-directional communication to provide an integrated control device.

Referring now to FIG. 10, the data received by the tactile array unit 10 need not be visual data but for example may provide tactile data for example from a sensor 80, for persons with a limb prosthesis or astronauts who must wear heavy gloves or operators of remote manipulators. The tactile data may include information about shape, shear forces, pressure and slip. One promising tactile sensor employs an elliptically shaped elastomeric membrane filled with a clear fluid the inner surface of the membrane is imprinted with a pattern so that deformation of the membrane by touching an object deforms the pattern in a way detectable by a camera aimed at the membranes inner surface. Gloves for leprosy patients with insensate hands or insoles for diabetic patients with insensate feet can be used with the present invention where the tactile data is conveyed to the mouth. The present invention may accept tactile data from a penile sheath for spinal cord injured patients who have lost sexual sensation.

The tactile data may be received by processing electronics 82, for example, a microprocessor processing the image from the camera system described above, and then transmitted by transceiver 84 to the tactile array unit 10. In order to provide an integrated mouth-based controller, the tactile array unit 10 may include one or more mouth-based sensors 79 that may be activated by the tongue 26 (not shown). In its simplest form the sensors 79 are conventional mechanical switches such as membrane switches incorporated into the material of the plate 14 but may also be electronic sensors detecting tongue placement using conventional impedance sensing techniques. The signal output from the sensors 80 of the tactile array unit 10 may be received by the transceiver 84 and conveyed through the processing electronics 82 to an actuator 86 such as a robot hand. Such a system could provide, for example, control of a robotics hand for persons with quadriplegia where the sensor 80 is one or more tactile sensors and the actuator is one or more robot axis motors.

The mouth-based sensors 79, in the alternative, may detect mouth chemistry using techniques known in the art, and may be combined with the tactile array unit 10 of the present invention to provide the user with an indication of blood levels of Nitrogen or $CO_2$ or the like, such as may be useful for divers.

When a camera is the input sensor to the tactile array unit 10, it need not be limited to a visible light range but may be a night vision camera or infrared vision camera (for example, for pilots or drivers) where bypassing the retina in favor of the tongue eliminates retinal delay. Image or non-image data may be used to augment visual information received by sighted individuals for example in infrared regions, ultrasonic or radar images for avionics and the like. Nor must the input be conventional sensory type inputs such as vision or touch or sound but may be fundamental data, for example, such as navigational direction and orientation for scuba divers and the like prone to becoming disoriented. For military purposes, the mouth-based HMI of the present invention relieves over-dependence on the visual pathways and may have as an input "take immediate action" indicators, such as those from collision avoidance systems in aircraft, or may provide expanded "peripheral vision" about enemy planes or missiles approaching from the side or rear. General communication functions could be provided through such an HMI for secret communications.

A number of other applications are possible for the present invention including aiding drivers in fog or race car drivers who need faster response times. On a more prosaic level, the tactile array unit may be used to augment video game output or provide for communication in very noisy environments or where sound is not permitted and for operation of machinery requiring extensive use of the hands such as crane operators or those manipulating contaminated nuclear materials.

The above description has been that of a preferred embodiment of the invention. It will occur to those that practice the art that many modifications may be made without departing from the spirit and scope of the invention. For example the scanning approach of the electrodes may be replaced with a simultaneous excitation of electrodes 18 when the continuous ground plane is used. Likewise although electronic stimulation is preferred, other forms of stimulation may be appropriate for use on the tongue should technology allow its miniaturization such as vibration-type stimulators.

In order to apprise the public of various embodiments that may fall within the scope of the invention the following claims are made.

We claim:

1. A tactile stimulation array for receiving a spatially encoded signal for a tongue comprising:
   a mouth part sized and adapted to be received and stabilized within a mouth;
   an electrode array of conductors positioned over an array area of a lower surface of the mouth part adapted to be in contact with the tongue when the mouth part is received within the mouth;
   an input for receiving the spatially encoded signal;
   excitation circuitry communicating with the input and the conductors of the electrode array so as to energize with a stimulating electrical signal referenced to a ground at least one conductor of the electrode array as a stimulating conductor according to the input for receiving the spatially encoded signal and to connect at least one other conductor of the electrode array as a ground conductor to the ground so as to provide a ground plane extending over substantially all of the array area outside the stimulating conductor.

2. The tactile stimulation array for the tongue as recited in claim 1
   wherein the conductors of the electrode array include a conductive sheet having apertures through which second conductors are exposed and wherein the excitation circuitry connects the conductive sheet to the ground as the ground conductor and connects at least one of the second conductors to the stimulating electrical signal as the stimulating conductor.

3. The tactile stimulation array for the tongue as recited in claim 1
   wherein the conductors of the electrode array include an array of conductive elements and wherein the excitation circuit connects at least one of the conductive elements to the stimulating electrical signal as the stimulating conductor and connects remaining of the conductive elements to the ground as the ground plane.

4. The tactile stimulation array for the tongue as recited in claim 1
   wherein the excitation circuitry includes a plurality of solid-state switches connecting a pole alternatively to the stimulating electrical signal or the ground and wherein each stimulating electrode is connected to a different solid state switch.

5. The tactile stimulation array of claim 1 wherein the stimulating electrical signal is a predetermined current value.

6. The tactile stimulation array of claim 1 wherein the stimulating electrical signal is a predetermined voltage value.

7. The tactile stimulation array of claim 1 wherein the stimulating electrical signal is a pulsatile electrical signal having variable characteristics selected from the group consisting of: pulse height, pulse width, the interval between pulses, the number of pulses in a burst, the interval between bursts.

8. The tactile stimulation array of claim 1 wherein the spatially encoded signal includes a plurality of data points having defined locations and magnitudes and wherein the excitation circuitry applies energies to the stimulating conductors having corresponding locations with the data points according to a function having the data point magnitude as a range and a value selected from the group consisting of: pulse amplitude, pulse duration and pulse frequency.

9. The tactile stimulation array of claim 8 wherein the spatially encoded signal is an image signal comprised of pixels having locations in the image and magnitudes corresponding to pixel intensities.

10. The tactile stimulation array of claim 1 wherein the mouth part includes an upwardly concave plate supporting on its lower surface the electrode array of conductors and sized and adapted to fit within the hard palate of a human mouth.

11. The tactile stimulation array of claim 10 wherein the upwardly concave plate is flanked on its lateral edges by bite bars, whereby the mouth part is adapted to be stabilized within the mouth by a pressing of the bite bars between the teeth.

12. The tactile stimulation array of claim 10 wherein the upwardly concave plate is flanked on its lateral edges by wire retaining elements adapted to be attached to the teeth, whereby the mouth part is adapted to be stabilized within the mouth against the teeth.

13. The tactile stimulation array of claim 1 wherein the electrodes are substantially coplanar with the lower surface of the mouth part.

14. The tactile stimulation array of claim 13 wherein the lower surface of the mouth part and the electrodes are formed as a flexible printed circuit board.

15. The tactile stimulation array of claim 1 wherein the mouth part is a nipple sized and adapted to be stabilized within the mouth of a sucking infant.

16. The tactile stimulation array of claim 1 wherein the array is a substantially rectilinear grid.

17. The tactile stimulation array of claim 1 wherein the input is a receiver communicating with the excitation circuitry and receiving the spatially encoded signal as a radio wave.

18. The tactile stimulation array of claim 1 wherein the mouth part includes a chamber holding the excitation circuitry.

19. The tactile stimulation array of claim 18 wherein the excitation circuitry is battery powered and wherein the mouth part includes a chamber holding a battery in communication with the excitation circuitry.

20. The tactile stimulation array of claim 5 wherein the mouth part includes at least one tongue actuable electrical switch.

* * * * *